United States Patent [19]

Thorburn et al.

[11] 3,963,391

[45] June 15, 1976

[54] METHOD AND APPARATUS FOR CONTROLLING SPEED AND TORQUE OF HAND HELD AIR DRIVEN VANE TYPE MOTORS

[76] Inventors: Fred E. Thorburn; T. Michael Thorburn, both of 13117 111th Place NE., Kirkland, Wash. 98052

[22] Filed: Nov. 21, 1974

[21] Appl. No.: 525,959

[52] U.S. Cl. .............................. 418/270; 74/478; 91/457; 137/596; 173/163; 251/295; 32/22
[51] Int. Cl.² ...................................... F04C 15/02
[58] Field of Search ............. 415/1, 20, 503; 32/22; 173/163; 137/596, 362; 418/270; 91/454, 465, 457; 251/295; 74/560, 478, 478.5, 512

[56] References Cited
UNITED STATES PATENTS

| | | | |
|---|---|---|---|
| 2,382,591 | 8/1945 | Warren | 91/465 |
| 2,505,333 | 4/1950 | Mead | 251/295 |
| 2,905,149 | 9/1959 | Swanson | 418/270 |
| 3,054,187 | 9/1962 | Staunt | 32/27 |
| 3,648,968 | 3/1972 | Reid et al. | 251/295 |
| 3,712,386 | 1/1973 | Peters | 173/163 |
| 3,752,241 | 8/1973 | Bent | 173/163 |
| 3,827,834 | 8/1974 | Kakimoto | 418/270 |

FOREIGN PATENTS OR APPLICATIONS

| | | | |
|---|---|---|---|
| 1,276,864 | 9/1968 | Germany | 32/22 |
| 1,115,165 | 5/1968 | United Kingdom | 418/270 |

*Primary Examiner*—Carlton R. Croyle
*Assistant Examiner*—O. T. Sessions
*Attorney, Agent, or Firm*—Roy E. Mattern, Jr.

[57] ABSTRACT

A method and apparatus for controlling speed and torque of hand held air driven vane type motors is available in several embodiments. For example, one embodiment is used in tool and die work and another embodiment is used in dental work. In reference to the latter, a foot operated control regulates the speed of an air driven handpiece, driving in turn various tools such as cutters and drills as they are generally used in a dental laboratory, by regulating the flow of compressed air both to and from the handpiece. Application of an operator's foot pressure on a floor level foot control, simultaneously depresses two valves which control the flow of compressed air. One valve controls the flow of compressed air from its source to the handpiece, and one valve controls the release into the atmosphere of compressed air from the handpiece. Release of pressure on the foot control returns the two valves, utilizing spring forces, to their original position cutting off the flow of compressed air both to and from the handpiece. By this control of the flow of compressed air to and from the handpiece, an immediate higher torque is available at low and median speed ranges.

1 Claim, 10 Drawing Figures

METHOD AND APPARATUS FOR CONTROLLING SPEED AND TORQUE OF HAND HELD AIR DRIVEN VANE TYPE MOTORS

BACKGROUND OF THE INVENTION

Fluid driven handpieces have been used previously for many purposes and in reference to dental operations, they have been used for grinding, drilling, cutting, and polishing teeth and dental pieces. Among the controllers used by others for regulating the speed of such handpieces are those illustrated and described by James C. Martin in his U.S. Pat. No. 3,568,318 and by Ulf Martin Christian Apelskog and Lennart Erik Idoft Gidlund in their U.S. Pat. No. 3,567,330. In both of these previously designed controllers, the speed of the handpiece is controlled solely by regulating the release to the atmosphere of compressed air upstream of the air motor. As less of the compressed air is released, a greater air pressure is placed on the air motor and the greater is its speed. In Martin's patent the amount of air pressure on the air motor is controlled by the selectable movement of an operator's thumb over and against portions of an external bleed off orifice of an air line, otherwise delivering all the air to an air motor. When a load is applied on the handpiece during operation, a higher torque is produced by increasing the thumb coverage of the external bleed off orifice.

In Apelskog and Gidlund's patent, the air pressure applied to the air motor of the handpiece is preset, through the combined use of an air reduction valve and an electronically operated air bleed off control valve located upstream of the fluid motor. To prevent the speed of the handpiece from slowing down when a load is placed upon the forming tool being driven by the handpiece air motor, during its operation, magnets are attached to the rotating turbine of the air motor to initiate the creation of impulses monitored by the electronic control unit. It in turn operates to maintain the air turbine's rotational speed. In response to a reduced rotational speed, the electronic control unit will close the air bleed off control valve a proportionate amount, increasing the air flow and pressure directed to the air motor, thus producing a higher torque and returning the handpiece to its original higher speed.

Although these prior controllers result in the delivery of compressed air to provide a sufficiently high torque at high speed operations, at low speed operations there must be time allowed for the buildup of air pressure and flow to create the amount of torque and/or speed that is wanted. Therefore, there remained a need for a speed controller, which could provide compressed air to a handpiece to obtain greater available torque at low speed operation, and medium speed operation. This invention overcomes these disadvantages, by applying full air pressure to the handpiece at all start up times and thereafter during operations to obtain the higher torques needed in the low and median speed ranges, by using two valves, one valve controlling compressed air flow to the intake and the other valve controlling air flow from the exhaust of the air driven motor of the handpiece. Essentially at all times the method involves supplying full line pressure and the full volume air to the intake of the vane type air motor, and thereafter controlling its speed by regulating the flow of exhaust air leaving the air motor.

SUMMARY OF THE INVENTION

When using hand held air driven vane type motors, for example, in tool and die shops, machine shops, and dental laboratories, a problem often arises at low speed and at medium speed operations in obtaining and maintaining the desired amount of torque as work loads are applied to the tool being rotated by the air vane motor of a handpiece. In contrast by using this control device, the desired torque of the handpiece is obtained at low speeds and is continued at medium speeds and on through higher speeds of operation, improving the overall control of the handpiece and its selected tool, throughout a wide range of selected combined loadings and speeds of the rotating tools.

This foot operated control contains two valves operated simultaneously as the operator's foot pushes down on the control. One valve controls the inflow of compressed air to the handpiece. The other valve, being simultaneously moved, controls the exhaust of compressed air from the handpiece to the atmosphere. When the two valves are closed, the basic source of compressed air remains on the line.

As foot pressure is placed on the foot control by an operator, the two valves are simultaneously moved and depending on their preselected valve openings, compressed air is controlled, both as it enters and leaves the handpiece in which an air vane motor is being driven. By maintaining fully compressed air at the intake side of the handpiece at all operating times, higher torques are available from the air vane motor during all low and medium speed operations and of course are obtained at high speed operations. Thus no delays are encountered to build up the air pressure to provide the needed torque for low speed and medium speed operations. Yet if higher speeds are wanted further depression of the foot control components simultaneously moves the valves to obtain these higher speeds. Their preselected changeable valve openings properly control the admission and exit of compressed air to the vane motor of the handpiece so the desired combination of torque and speed is always acquired.

DESCRIPTION OF DRAWINGS

To explain the method and apparatus for controlling the speed and torque of hand held air driven motors, a preferred embodiment of a foot operated control to regulate the speed and torque of a compressed air driven vane motor of a dental laboratory handpiece, by controlling the flow of compressed air, and especially the flow from the air motor, is illustrated in the following figures, wherein.

DESCRIPTION OF A PREFERRED EMBODIMENT

A Typical Environment or Overall Assembly of a System

Figure 1:
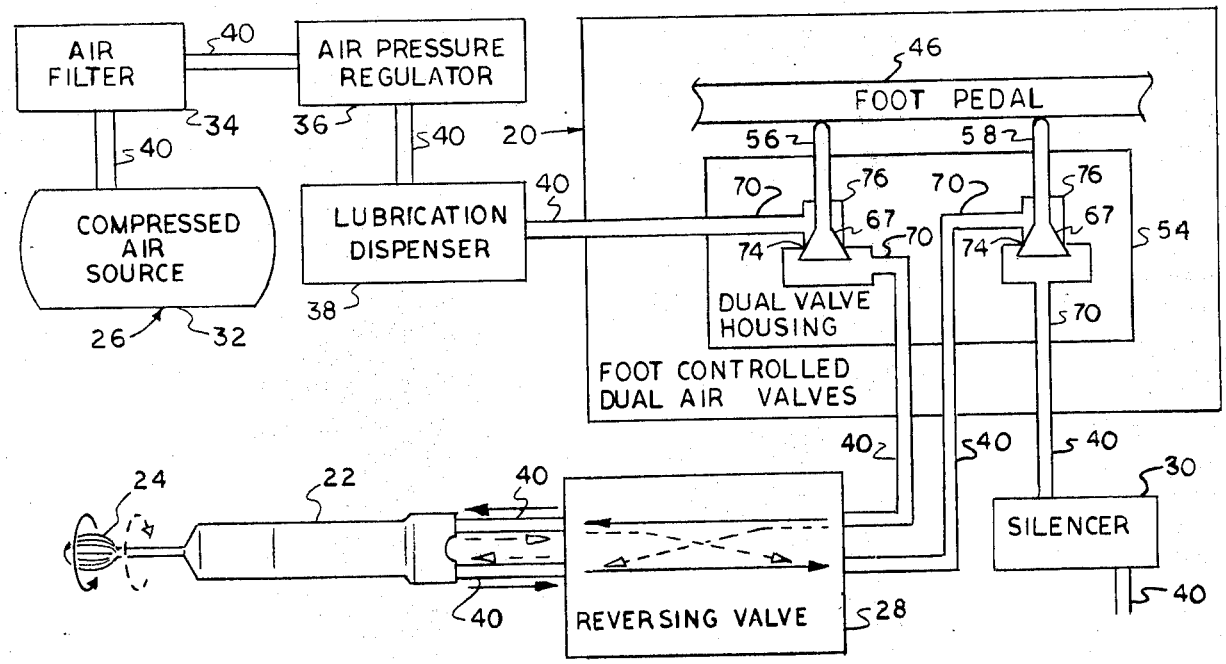
FIG. 1 is a schematic diagram of an overall preferred system, with flow and motion arrows, incorporating both the foot operated control and the handpiece and its tool, and also the conventional optionally selected components such as the air flow reversing valve, lubricant dispensor, air pressure regulator, air filter, compressed air source and exhaust muffler or silencer.

As viewed in FIG. 1, the foot operated control 20 for air driven handpieces 22 rotating dental laboratory tools 24, may be included in the illustrated typical environment or overall assembly of the system 26, wherein some of the components are optionally included, such as the air flow direction reversing valve 28 and muffler or silencer 30. Preferably, the other components, beyond the needed compressed air source 32, are generally included, such as the air filter 34, air pressure regulator 36, and lubricant dispensor 38. Throughout the system 26 between the components, the compressed air is directed through tubing 40.

A Handpiece Having Air Vane Motor for Rotating Dental Laboratory Tools

Although positive type air vane motors, many having oppositely located vanes tied together, are designed for assuming operational loads reasonably soon, most operational work in dental laboratories requires not only a fast response but also an immediate high torque power to support heavy cutting operations. Such vane motors, not shown in the drawings, are installed inside the handpieces 22, and the operation of the foot operated control 20 regulates the compressed air, so the fast response will also involve high torque power to rotate the dental laboratory tools 24.

Figure 2:
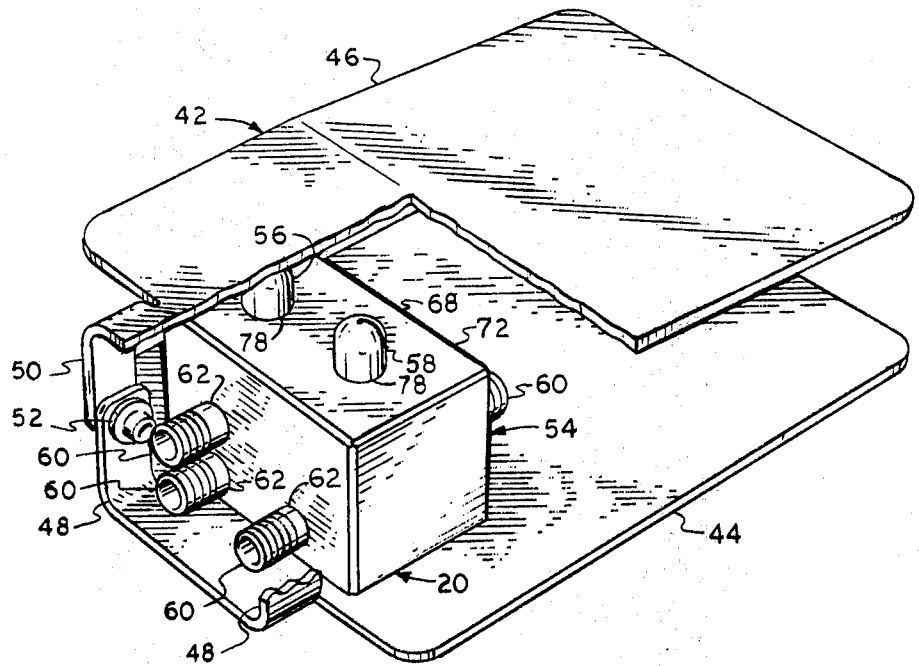
FIG. 2 is a perspective view, with portions broken away, of the foot operated control for the air driven handpiece rotating a dental laboratory tool.

A Foot Operated Control to Open an Air Valve Passing Compressed Air on to the Air Motor of the Handpiece, and to Open an Air Valve Allowing Compressed Air to Leave the Air Motor and be Exhausted Into the Atmosphere A preferred embodiment of the foot operated control 20 is illustrated in FIG. 2. The overall mechanism 42 for receiving and distributing the foot pressure comprises a base member 44 for placement on a floor and an upwardly spaced foot receiving member 46 pivotally secured to the base member 44. Upwardly extending dual arms 48 secured to the base member 44 overlap downwardly extending dual arms 50 secured to the foot receiving member 46, and near their extremities they are pivotally secured together using fasteners 52.

A housing 54 is secured to the base member 44 below the pivotal foot receiving member 46 and adjacent to the overlapping dual arms 48, 50. Two air flow control valves one, 56, for controlling supply air and the other, 58, for controlling exhaust air, are positioned in the housing 54 while extending partially above the housing when the foot receiving member 46 is not bearing any load. When however, an operator's foot is pressed downwardly on the foot receiving member 46, the air flow control valves 56 and 58 are moved downwardly respectively to supply compressed air to the air vane motor of the handpiece 22 and to exhaust air leaving the handpiece 22 into the atmosphere. Nozzle like fittings 60 are threaded into orifices 62 on the housing 54 to receive tubing 40 bringing compressed air to the housing 54, tubing 40 directing air from the housing to the handpiece 22, tubing 40 bringing air from the air motor of the handpiece back to housing, and possibly tubing 40, the muffler 30, and/or the orifice 62 or nozzle 60 per se releasing the compressed air coming, from the air motor in the handpiece 22, into the atmosphere. Optionally a muffler or silencer 30 is used during the exhausting of the compressed air.

Figure 5:
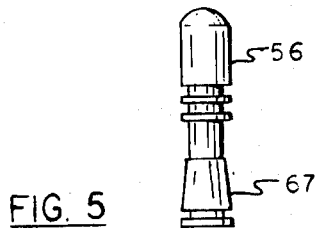
FIG. 5 is a side elevation of one of the air flow control valves before its sealing rings are installed.
Figure 6:
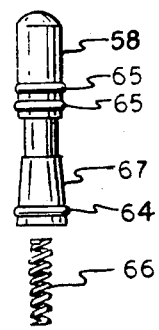
FIG. 6 is a side elevation of one of the air flow control valves after its sealing rings are installed and it is arranged with its return compression spring.

The Interior of the Housing of the Foot Operated Control and How the Valves are Formed to Control the Compressed Air Flow When They are Moved In FIG. 5 a valve either 56 or 58, which are alike, without sealing rings 64 and 65 is shown, and in FIG. 6, a valve 56 or 58, with sealing rings 64 and 65 is illustrated. The sealing ring 64, often referred to as an O-ring, is positioned near the bottom respectively of both valves 56 and 58 and serves as the main seal with respect to the compressed air flow passing through the housing 54 enroute to or from the handpiece 22. Just above this sealing ring 64 is the frusto conical portion 67 respectively of both valves 56 and 58, which in conjunction with the interior structures of the housing 54 varies the size of the circumferential valve opening, thereby further controlling the compressed air flow. To keep compressed air from unwantedly departing upwardly and out of the top of the housing 54, the dual spaced sealing rings 65 are positioned around the upper portions respectively of both valves 56 and 58. Also included in FIG. 6 is one of the two compression springs 66 used to respectively move the air flow control valves 56, 58, to their closed positions.

Figure 3:
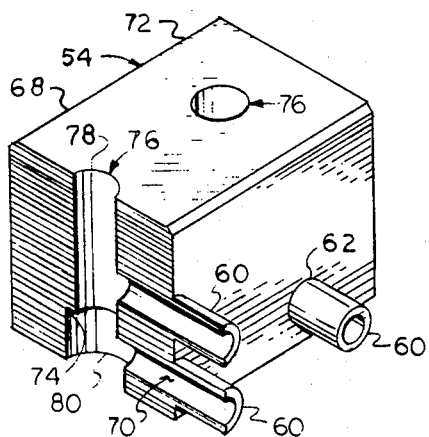
FIG. 3 is a perspective view of portions of the foot operated control showing the housing with portions removed to illustrate the interior cylindrical volumes which receive one of the air flow control valves regulating compressed air coming in through one passageway from a compressed air source and having through another passageway to go on to an air vane motor of a handpiece, when the air flow control valve is opened upon depression of the foot operated control.
Figure 4:
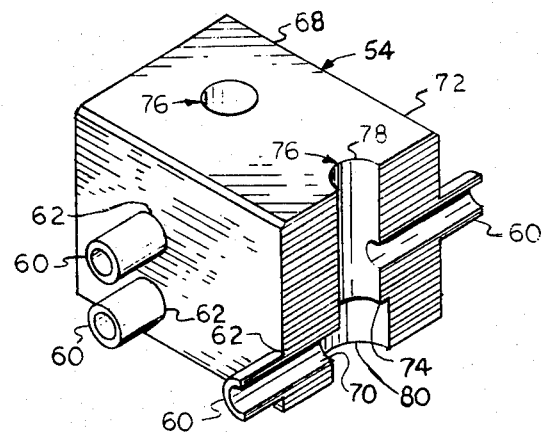
FIG. 4 is a perspective view of portions of the foot operated control showing the housing with portions removed to illustrate the interior cylindrical volumes which receive the other air flow control valve regulating compressed air leaving the air vane motor of a handpiece to be discharged to atmosphere, optionally through a muffler, when this other air flow control valve is opened upon depression of the foot operated control.
Figure 7:
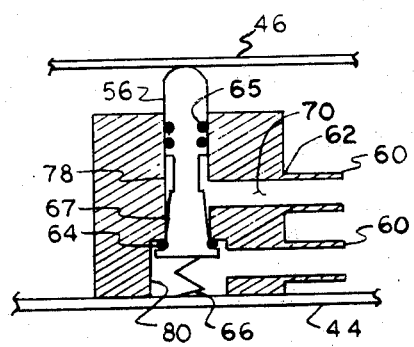
FIG. 7 is a schematic elevational view of portions of the foot control to indicate the position of one air flow control valve keeping the supply of otherwise oncoming compressed air from reaching the air vane motor of a handpiece, before foot pressure is applied.
Figure 8:
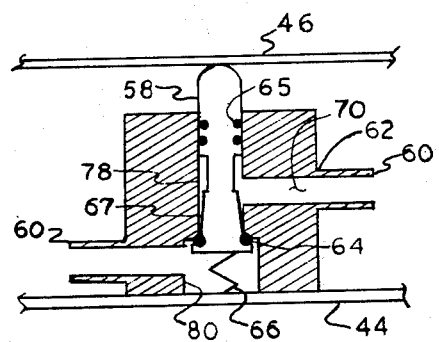
FIG. 8 is a schematic elevational view of portions of the foot control to indicate the position of the other air flow control valve keeping the compressed air in the handpiece from exhausting into the atmosphere.
Figure 9:
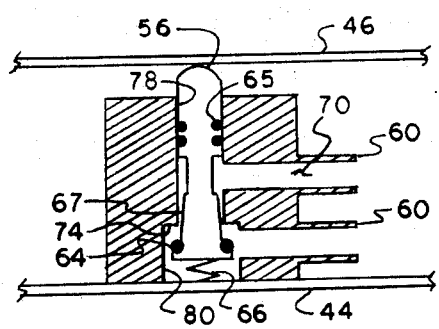
FIG. 9 is a schematic elevational view of portions of the foot control to indicate the position of one air flow control valve which is open allowing the oncoming compressed air to reach the air vane motor of the handpiece.
Figure 10:
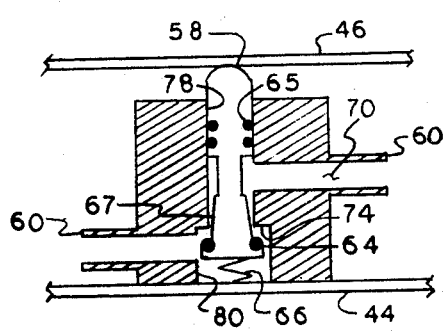
FIG. 10 is a schematic elevational view of portions of the foot conrol to indicate the position of the other air flow control valve which is open allowing the compressed air in the handpiece to exhaust into the atmosphere.

In FIGS. 3, 7 and 9, the interior volumes of the housing 54 are illustrated in reference to the portion 68 thereof, wherein the compressed air, coming from the compressed air source 32, is directed through passageways 70 and controlled by valve 56, enroute to the air vane motor of the handpiece 22. In FIGS. 4, 8 and 10, the interior volumes of the housing 54 are illustrated in reference to the portion 72 thereof, wherein the compressed air, leaving the air vane motor of the handpiece 22, is directed through passageways 70 and controlled by valve 58 enroute to an exhaust orifice 62, a nozzle like fitting 60, or a silencer or muffler 30 for discharge into the atmosphere.

In FIGS. 7 and 8, the foot receiving member 46 has not been depressed and the respective supply air control valve 56 and the exhaust air control valve 58 by action of their respective springs 66 are being held in their closed position. In FIGS. 9 and 10, the foot receiving member 46 has been depressed, as indicated by the motion arrows, and the respective supply air control valve 56 and the exhaust air control valve 58 have been moved downwardly against their spring forces so their sealing rings 64 clear the internal sealing portions 74 of the interior cylinders 76 of the housing 54. The sealing portions 74 are located at the transition structure between the small diameter portion 78 and the larger diameter portion 80 of the interior cylinder 76.

Other Possible Embodiments of the Foot Control

In regard to the preferred embodiment shown, throughout the FIGS. 1 through 10, the supply valve 56 and exhaust valve 58 are arranged side by side to be both directly moved by the foot receiving member 46. They are however, in another embodiment arranged in tandem one above the other having a common valve portion extending above a deeper housing to be directly moved by the foot receiving member 46. In another embodiment, the valve controlling the entry of compressed air into the intake of the vane type air motor is separate and hand controlled at any location such as on a work bench and the valve controlling the exhaust flow of compressed air from the outlet of the air motor is located in a foot operated control. In another embodiment there are two side by side foot depressible structures in the foot operated control, and a housing extends below both to position two sets of supply and exhaust valves. The interior passageways of the extended housing are formed, so upon the depression of one foot operated control portion, the air motor rotates in one direction, and upon the depression of the other foot operated control portion, the air motor rotates in the other direction.

The Principal Operating Advantage is Achieved by the Method of Controlling the Exhaust Air Flow as the Principal Intake Air Flow is Continued Essentially at Line Pressure All those persons who use and will be using air driven handpieces having vane type air motors to perform dental operations, tool and die operations, and other machine shop type operations, by using these foot operated controls in their various embodiments are assured the torque they need is available essentially from the outset and remains throughout, low, medium and high speed operations. At all times, the exhaust air flow leaving the air motor is controlled to change the operating speeds of the revolving tools, while still maintaining the various high level torque capabilities desired, especially at low and medium speeds and continuing on through higher speed operations.

We claim:

1. A foot operated control for placement on a floor and then to be actuated upon the pivotal movement of a person's foot being pivoted about a heel, to simultaneously regulate the flow of compressed air to and from a vane type air motor mounted within a handpiece for holding and driving rotatable dental laboratory tools, comprising:

a. a rectangular base for placement on the floor, having at one end spaced upstanding hinge supports, integrally derived from the said base following the formation of inwardly directed opposed partial cuts which terminate at respective ninety degree bends where these upstanding hinge supports then commence, and holes are formed at the upper terminus of each upstanding hinge support;

b. a rectangular cover for pivotal hinge attachment to the rectangular base, having at one end spaced depending hinge supports, integrally derived from the said cover following the formation of inwardly directed opposed partial cuts which terminate at respective ninety degree bends where these depending hinge supports then commence, and holes are formed at the lower terminus of each depending hinge support;

c. pivotal fastening subassemblies to join together the respective pairs of spaced upstanding and depending hinge supports which are respectively integral with the rectangular base and rectangular cover;

d. a rectangular housing having internal formed spaces for two valve assemblies and for compressed air passageways leading to and from the respective valve assemblies secured to the rectangular base adjacent the upstanding and depending hinge supports and extending only a partial distance along the said base, and of a height less than the assembled height of the upstanding and depending hinge supports, to thereby permit an unobstructed pivotal motion of the rectangular cover with respect to the rectangular base upon the pivotal movement of a person's foot being pivoted about a heel, before such movement is ultimately limited by the top of the rectangular housing;

e. a first spring positioned valve assembly installable from below within a vertical passageway of the rectangular housing, having sealing means, a compression spring, and a valve stem, which, when raised by the spring, contacts the rectangular cover to be depressed upon the pivotal movement of the said cover, said first valve stem movement interconnecting compressed air passageways respectively bringing compressed air from a compressed air source and delivering compressed air to a vane type air motor of a handpiece;

f. a second spring positioned valve assembly installable from below within a vertical passageway of the rectangular housing, having sealing means, a compression spring, and a valve stem, which, when raised by the spring contacts the rectangular cover to be depressed upon the pivotal movement of the said cover, such second valve stem movement interconnecting compressed air passageways respectively bringing compressed air from the exhaust side of a vane type air motor of a handpiece and directing it to an exhaust to atmosphere discharge opening of the said housing; and four respective projecting connectors insertable in the rectangular housing to receive respective compressed air lines bringing air to and conducting air away from the said housing, as the respective air flows are controlled by the said first and second valve assemblies.

* * * * *